United States Patent [19]

Zarlenga, Jr. et al.

[11] Patent Number: 5,874,251
[45] Date of Patent: Feb. 23, 1999

[54] **DNA ENCODING THE *TAENIA CRASSICEPS* TEN KILODALTON ANTIGEN**

[75] Inventors: Dante Sam Zarlenga, Jr., Ellicott City; Marcia Louise Rhoads, Fulton, both of Md.

[73] Assignee: The United States of America as represented by the Secretary of Agriculture, Washington, D.C.

[21] Appl. No.: 648,496

[22] Filed: May 15, 1996

Related U.S. Application Data

[63] Continuation of Ser. No. 959,010, Oct. 9, 1992, abandoned, which is a continuation-in-part of Ser. No. 717,235, Jun. 18, 1991, abandoned.

[51] Int. Cl.$^6$ ............... C12N 15/12; C12N 15/30; A61K 39/002
[52] U.S. Cl. ............ 435/69.3; 435/97; 435/172.3; 435/235.1; 435/252.3; 435/252.33; 435/254.11; 435/325; 435/358; 435/362; 435/364; 435/365; 536/23.5; 536/23.7; 530/300; 530/350; 935/18; 935/27; 935/31; 935/41; 935/56; 935/57; 935/58; 935/67
[58] Field of Search ............ 435/69.3, 97, 172.3, 435/235.1, 252.3, 252.33, 254.11, 325, 358, 362, 364, 365; 536/23.5, 23.7; 530/300, 350; 935/18, 27, 31, 41, 56–58, 72, 70, 73, 67, 68; 424/184.1, 185.1, 265.1, 266.1

[56] References Cited

PUBLICATIONS

Salgaller et al. Cancer Immunol. Immunother. 39:105–116, Aug. 1994.
Lazar et al. Mol. Cell Biology 8:1247–52, Mar. 1988.
Burgess et al. J Cell Biol. 111:2129–38, Nov. 1990.
Hayunga, E. G et al. Am.J. Vet.Res. 52(3):462–470 (1991).
Ellis, R.W. "New technologies for making vaccines" In Vaccines Plotkin & Mortimer Eds. W.B. Saunders Co. (1988).
Bowies, J.V et al. Science 247:1306–1310 (1990).
Keemar, V. et al. Proc. Natl. Acad. Sci USA 87:1337–1341 (1990).
Honwell, M.J. et al. Msl. Biochem. Parasit. 28:21–30 (1988).
Kamángá–Sollo, E. et al., *Proc. Am. Assoc. Vet. Parasitol.* 31:31 (1986).
Rhoads, M. et al., *Vet. Arch.* 57(3): 143–150 (1987).
Diwan et al., *Am. J. Trop. Med. Hyg.* 31: 364–369 (1982).
Espinoza et al., *Cysticercosis. Present State of Knowledge and Perspectives.* 163–170, Academic Press, New York (1982).
Coker–Vann et al., *Trans. Roy. Soc. Med. Hyg.* 78:492–496 (1984).
Gottstein et al., *Am. J. Trop. Med. Hyg.* 35: 308–313 (1986).
Gottstein et al., *Trop. Med. Parasitol.* 38: 299–303 (1987).
Nascimento et al., *J. Clin. Microbiol.* pp. 1181–1185 (1987).
Sanger et al., *Proc. Natl. Acad. Sci.* USA, 74: 5463–5467 (1977).
Kraft et al., *Biotechniques* 6: 544–546 (1988).
Glover, D. Ed., *DNA Cloning*, vol. II, pp. 45–66, IRL Press (1985).
Kamanga–Sollo et al., *Proc. Am. Assoc. Vet. Res.* 48: 1206–1210 (1987).
Okayama et al., *Methods of Enzymol.* vol. 154: 3–28 (1987).
Aviv et al., *Proc. Natl. Acad. Sci.* USA 69: 1408–1412 (1972).
Gubler et al. *Gene*, 25: 263–269 (1983).
Watson et al., *DNA Cloning*, vol. I, Ed. D.M. Glover, IRL Press, Oxford pp. 79–88 (1985).
Young R. et al., *Proc. Natl. Acad. Sci.* USA 80: 1194–1198 (1983).
Veira, J. et al., *Gene* 19: 259–268 (1982).
Guan et al., *Gene* 67: 21–30 (1987).
Hanahan, *J. Mol. Biol.* 166: 557–580 (1983).
Rigby et al., *J. Mol. Biol.* 113: 237 (1977).
Dame, J. et al., *Molecular and Biochemical Parasitology* 8: 263–279 (1983).
Southern, E., *J. of Molecular Biology* 98: 503–517 (1975).
Davis, L. et al., *Basic Methods in Molecular Biology*, Elsevier Science Publishing Company, Inc., pp. 143–146 (1986).
Howell, M. et al., *Molecular and Biochemical Parasitology* 28: 21–30, (1988).
Craig et al., *Zeitschrift fur Parasitenkunde* 61: 287–297 (1980).
Geerts et al., *Res. Vet. Sci.* 30: 288–293 (1981).
Rhoads, M. et al., *J. Parasitol.*, 71: 779–787 (1985).

*Primary Examiner*—Anthony C. Caputa
*Attorney, Agent, or Firm*—M. Howard Silverstein; Joseph A. Lipovsky; John D. Fado

[57] ABSTRACT

Antigens derived from *Taenia crassiceps* have been isolated which have specificity and sensitivity in their reactivity with antibodies against *Taenia saginata* and *Taenia solium*. These antigens may therefor be used in diagnostic testing for the serological screening of livestock for cysticercosis, rather than relying upon methods involving dissection and visual examination.

14 Claims, 3 Drawing Sheets

DNA ENCODING THE *TAENIA CRASSICEPS* TEN KILODALTON ANTIGEN

This application is a continuation of application Ser. No. 07/959,010, filed Oct. 9, 1992, now abandoned, which is a continuation-in-part of application Ser. No. 07/717,235, filed Jun. 18, 1991, now abandoned.

BACKGROUND OF THE INVENTION

1. Field of the Invention

The present invention relates to purified and isolated antigens for the detection of bovine or swine cysticercosis and methods of synthesis of recombinant antigens using genetic engineering techniques.

2. Description of the Art

Cysticercosis is a parasitic disease of cattle and swine caused by the larval (cyst) stage of the tapeworm *Taenia saginata* in cattle and *Taenia solium* in swine. Ingestion by man of viable larvae in undercooked meat results in intestinal tapeworm infection (taeniasis). The meat of these animals contains larvae that mature, in the intestinal tract, into adults that burrow into the mucosa and at the same time attach themselves to the bowel wall with scolices which bear hooks. The mature worm then progressively develops to lengths of 3 to 6 meters (10 to 20 feet). Clinical manifestations of the intestinal infection arise from the physical mass of the worms, the trauma to the intestinal mucosa, reaction to worm metabolites, and competitive uptake of nutrition. Of particular concern is taeniasis caused by the swine tapeworm (*T. solium*) which has the potential to lead to human neurocysticercosis, with serious, debilitating and possibly fatal consequences. As these tapeworms pose a dramatic health risk, infected carcasses discovered during inspection at the slaughter house are condemned as a matter of public policy.

Present inspection of livestock or meat for cysticercosis infection requires dissection and visual examination of specimens, a tedious, time-consuming and labor-intensive practice. The direct meat inspection is done using organoleptic means based on prescribed procedures designed to optimize detection of lesions. These postmortem examinations for cysts are extremely insensitive. It is estimated that organoleptic inspections for metacestode cysts performed at the time of slaughter misdiagnose in excess of 25% of infected animals as falsely negative. The detection of *Taenia saginata* and *Taenia solium*, the causative agents of cysticercosis, continue to pose large economic losses and serious health concerns in a number of countries, including the United States.

As yet, serological diagnostic tests for screening livestock have not been available due to the lack of specific and sensitive antigen reagents. Previous efforts to develop specific and sensitive antigens have not met with success. Given the moderate level of host antibody responses to cestode infections and the low numbers of cysts often associated with naturally-infected animals it was necessary to develop a highly sensitive and specific test.

Antigen reagents which have been evaluated by the ELISA method for the detection of *T. saginata* antibodies include an adult cestode extract which is reported to have strong cross-reactivity with antibodies to *Fasciola hepatica*, a common trematode parasite of cattle [Craig et al., *Zeitschrift fur Parasitenkunde* 61:287–297 (1980)].

A de-lipidized saline extract of the larval stage of the heterologous cestode *Taenia crassiceps* was evaluated as an immunodiagnostic antigen and though it exhibits a high degree of specificity for *T. saginata* antibodies (4.3% false-positive reaction) it has an unacceptably low degree of sensitivity for antibodies in both naturally (62% false-negative reaction) and experimentally infected animals [Geerts et al, *Res. Vet. Sci.,* 30:288–293 (1981)].

A heterologous antigenic fraction purified from *Taenia hydatigena,* termed ThFAS, demonstrated reliable detection of *T. saginata* antibodies using the enzyme linked-immunosorbent assay (ELISA) where the specific immunodiagnostic reactivity of this fraction was associated with a 10 kDa protein. See Rhoads, M. et al.,*J. Parasitol.* 71:779–787 (1985); Kamanga-Sollo, E. et al., *Proc. Am. Assoc. Vet. Parasitol.* 31:31 (1986); and Rhoads, M. et al., *Vet. Arch.,* 57(3)143–150 (1987). As ThFAS is derived from naturally-occurring sheep cestodes, limitations have been encountered in obtaining the antigen in sufficient quantities and purity for use in a viable commercial test. Obtaining the homologous antigen from *T. saginata* cysts presents a problem since the muscle cysts and hence the mRNA from *T. saginata,* is difficult to purify free of host material. Consequently, the identification of an alternative source is necessary.

Efforts to develop an assay for the diagnosis of cysticercosis in humans has also been less than completely successful. Currently, the ELISA method shows the highest accuracy of immunodiagnosis for human cysticercosis. Using either a crude extract of swine cysticerci as an antigen or a purified fraction thereof (antigen B), antibodies were detected by ELISA in sera or cerebrospinal fluid (CSF) in only 70 to 80% of the clinically diagnosed cases [Diwan et al., *Am. J. Trop. Med. Hyg.* 31:364–369 (1982); and Espinoza et al., *Cysticercosis. Present State of Knowledge and Perspectives,* 163–170, Academic Press, New York (1982)]. In addition, non-specificity has been demonstrated using this method (Coker-Vann et al., *Trans. Roy. Soc. Med. Hyg.* 78:492–496 (1984)). However, false-positive reactions can be eliminated by combining ELISA with an immunoblotting technique [Gottstein et al, *Am. J. Trop. Med. Hyg.* 35:308–313 (1986) and *Trop Med. Parasitol.* 38:299–303 (1987)]. Recently, an ELISA using any one of three purified proteins isolated from the scolex of *T. solium* metacestodes by monoclonal antibody-immunoaffinity chromatography was able to detect 100% of the patients with cysticercosis and showed no false-positives (Nascimento et al 1987). In all of these human cysticercosis assays, the antigenic reagent was obtained from the homologous cestode, *T. solium*. Furthermore, to achieve accurate and reliable assays it is necessary to use additional expensive and time-consuming techniques.

These techniques would be completely unacceptable as a screening tool for the inspection of livestock or meat. An acceptable screening method must be capable of diagnosing cysticercosis in livestock or meat with a high degree of both sensitivity and specificity while remaining cost effective. Such an immunoassay screening method requires an appropriately reactive antigen. Since availability of antigen is a major limiting factor in diagnostic test development and production, reliable sources of antigen must be secured and the antigen must be available in quantities sufficient to support field trials and large scale test implementation.

SUMMARY OF THE INVENTION

It is an object of the present invention to overcome the deficiencies in the prior art, such as indicated above.

It is another object of the present invention to isolate and purify a diagnostic antigen having specific and sensitive antigenicity for *Taenia saginata* and/or *Taenia solium* (i.e., reactivity for antibodies against *T. saginata* and/or *T. solium*). It is an additional object of the present invention to isolate and purify an antigen for use in an immunoassay for the diagnosis of bovine and swine cysticercosis without said antigen having cross-reactivity with antibodies to other common bovine and swine parasites.

In one embodiment of the invention, the antigen is immunologically distinct from other common bovine and/or swine parasites, in particular *Fasciola hepatica*. The antigen may be extracted from *Taenia crassiceps*. In a further embodiment of the invention, the antigen is a protein isolated using ultracentrifugal density flotation. In yet a further embodiment the antigen is a 70% ammonium sulfate-soluble protein and has an apparent molecular weight of 10,000 by SDS-PAGE.

It is a further object of the present invention to isolate and identify a DNA molecule having a DNA sequence coding for a homologous segment of a diagnostic antigen having specific and sensitive antigenicity for *Taenia saginata* and/or *Taenia solium*.

In one embodiment of the present invention the DNA molecule codes for a homologous segment of an antigen having the desired immunodiagnostic characteristics. In another embodiment of the present invention the DNA molecule has a specific nucleotide sequence, preferably the sequence in Table I. In yet another embodiment of the present invention the DNA molecule comprises a DNA sequence made from the mRNA isolated from *Taenia crassiceps*.

It is yet another object of the present invention to use genetic manipulation to obtain polynucleotides comprising a first nucleotide sequence for a diagnostic antigen in operable combination with a second nucleotide sequence.

In one embodiment of the present invention the first polynucleotide is a sequence for the isolated antigen or a homologous segment thereof, preferably for the sequence in Table I or gene TCA-2. In another embodiment of the present invention the second nucleotide codes for β-galactosidase or a fragment thereof. In a further embodiment of the present invention the second nucleotide comprises bacteriophage lambda gt 11 or the plasmids pUC18, or pIH821.

It is still another object of the present invention to use genetic manipulation to obtain a polynucleotide expression vehicle. In one embodiment the expression vehicle is a replicon, plasmid, bacteriophage, virus or hybrid thereof. In one embodiment the expression vehicle includes the operable combination of the polynucleotides, preferably the plasmid vector pTCA2.

It is a still further object of the present invention to use genetic manipulation to transform or transfect a host cell with an expression vehicle forming a cell line, preferably the cell line Y1090 and PR722.

Another object of the present invention is achieving a method of producing a purified antigen using transformed, transfected or infected host cells as a means of achieving mass production of antigens and thereby achieving an abundant and inexpensive antigen supply.

Yet another object of the present invention is achieving a purified recombinant diagnostic antigen which can be easily purified to homogeneity, in high quantitities and at relatively little expense without the need to use laboratory rodents for propagation of the diagnostic antigen.

In one embodiment of the present invention the purified recombinant diagnostic antigen is produced using the above discussed host cell line, preferably PR722. In another embodiment of the invention the purified recombinant diagnostic antigen is homologous to the purified and isolated antigen having *Taenia saginata* and *Taenia solium* antigenicity, preferably with the amino acid sequence of Table I or the antigen TCA-2 or TCA-2-MBP.

A still further object of the present invention is achieving accurate and reliable screening methods having improved efficiency of inspection procedures and reduced cost. In one embodiment of the invention the method is directed to the diagnosis of cysticercosis using the antigens of the present invention to form an immunocomplex with antibodies present in the sample to be tested and detecting the presence of the complex.

These and other objects and advantages of the instant invention will be more apparent from the following detailed description and exemplified embodiments, taken in conjunction with the accompanying drawings.

DETAILED DESCRIPTION OF THE INVENTION

Novel Diagnostic Antigens

Figure 1:
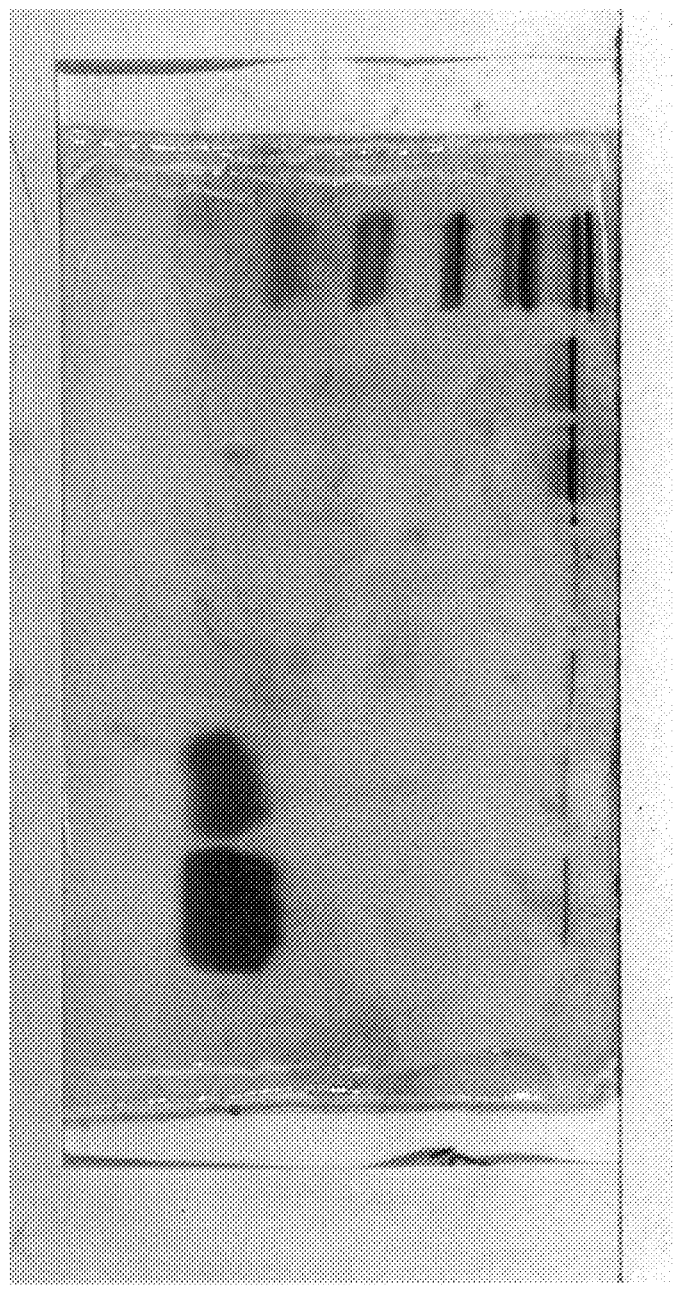
FIG. 1 is a SDS-PAGE of the diagnostic antigen isolated from *Taenia hydatigena*. Channel one contains standards; channels two and three contain the high molecular weight components of ThFAS which elute as Peak I by HPLC: and channels four and five contain the low weight components of ThFAS which elute as Peak II by HPLC.

The present invention provides for novel diagnostic antigens useful in the detection of bovine or swine cysticercosis. The antigens are extracted from *Taenia crassiceps* (TcAS) and have unexpectantly been found to react with both antibodies against *Taenia saginata* and *Taenia solium* with a high degree of sensitivity and specificity. *Taenia crassiceps* is a canine tapeworm that exists and can be maintained in rodents in the cyst stage (larval stage). Further, the antigen can be used to differentially diagnose bovine or swine cysticercosis due to the presence of *Taenia saginata* or *Taenia solium* from other commonly occurring parasites.

Unexpectedly, it has been found that polyclonal rabbit ThFAS antibodies cross-react with protein preparations from other parasites of the Taenia genus, including the antigen of the present invention prepared from cestode, *Taenia crassiceps*. The problem of obtaining pure cestode nucleic acids from *T. saginata* cysts, normally contaminated with bovine muscle tissue, can be circumvented using *T. crassiceps* metacestodes for parasite propagation within the peritoneal cavity of mice which allows isolation of protein free of integrated host tissue. However, this does not obviate the problem of using rodent models to generate parasites for antigen production.

ThFAS contains a group of high molecular weight proteins (65 to 77 kDa) and a low molecular weight protein of 10 kDa. The 10 kDa protein has been identified as the *T.*

*saginata*—reactive, immunodiagnostic component. TcAS contains a related 10 kDa protein that is recognized by anti-ThFAS serum; however, the high molecular weight ThFAS-cross-reactive proteins were not present in TcAS. Conversely, rabbit anti-TcAS specifically recognized the 10 kDa proteins (appearing as a doublet) in ThFAS and TsAS (antigenic fraction prepared from *Taenia saginata*), as well as the homologous antigen, TcAS, but did not crossreact with any high molecular weight antigens.

The 10 kDa and 70% ammonium sulfate-soluble protein fraction from *T. crassiceps* (TcAS) is obtainable in the present invention. The antigen can be isolated by ultracentrifugal density flotation using either ammonium sulfate at a specific gravity of 1.231 g/ml or NACl/KBr at 1.225 g/ml, followed by gel filtration under denaturing conditions (6M guanidine-HCl, 5% 2 Me and 100° C. heat). The resulting homogenous protein has a relative (or apparent) molecular weight of 10,000 by SDS-PAGE. The antigenic fraction has shown potential as an immunodiagnostic reagent for bovine cysticercosis.

The purified antigen can be employed in a method of diagnosing cysticercosis. In particular, the antigen can be employed in an immunoassay to detect the presence of antibodies to *Taenia saginata* or *Taenia solium* in a sample. The sample can be body fluids such as blood, urine, cerebrospinal fluid, or preferably serum. The presence of these antibodies can be used to diagnose cysticercosis. Although this method can be used to make the diagnosis in humans, it is particularly useful for testing cattle or swine, either as livestock or after slaughter.

Isolation of the purified antigen allows for the genes to be cloned, the DNA sequence to be determined and the amino acid sequence determined. The antigen may then be produced using gene cloning or recombinant DNA techniques.

DNA Sequence of Novel Diagnostic Antigen

Since availability of antigen is a major limiting factor in diagnostic test development and production, reliable sources of antigen must be secured prior to field trials and large scale test implementation. Mass production of antigen by in vitro synthesis offers an attractive solution to the antigen supply once the reactive antigen has been identified.

The DNA sequence of the novel diagnostic antigen can be determined using conventional techniques such as the dideoxy chain termination method of Sanger et al., *Proc. Nat. Acad. Sci. USA*, 74:5463–5467 (1977) as modified by Kraft et al., *Biotechniques* 6:544–546 (1988).

Using these genetic engineering techniques a DNA sequence which encodes the amino acid sequence of the homologous segment of the antigen isolated from *Taenia crassiceps*, can be generated. The phrase "homologous segment of the antigen" means an amino acid sequence sufficiently duplicative of the antigen of the present invention to allow the possession of the unique biological property of being able to bind antibodies against *Taenia saginata* and/or *Taenia solium*.

A cDNA expression library was constructed in the bacteriophage vector lambda-gt11 using poly A mRNA purified from *Taenia crassiceps* metacestodes in order to identify a recombinant antigen for the diagnosis of bovine cysticercosis. The cDNA library was screened with rabbit antiserum to ThFAS, and with bovine antiserum to *Taenia saginata*.

Primary screening of *T. crassiceps* cDNA clones with rabbit anti-ThFAS serum identified at least 32 strongly reactive plaques. The positive clones were plaque purified. One phage, designated lambda-TCA-2, lysogenized into *E. coli* strain Y1089, generated a β-galactosidase fusion protein with a relative molecular weight of 120 to 130 kDa and reacted specifically with cysticercosis-infected bovine sera. The clone contained a cDNA insert approximately 288 base pairs in length and reacted strongly with both antisera. The cDNA is encoded by a messenger RNA of approximately 450 bases in length.

Because of inefficient synthesis of the fusion protein, the 288 bp cDNA sequence from lambda-TCA-2 was subcloned into the plasmid pIH821 generating a 47 kDa maltose-binding fusion protein, designated TCA2-MBP. Affinity-purified TCA2-MBP reacted strongly with sera from cattle experimentally infected with *T. saginata* by both ELISA and Western blot analysis but did not cross-react with sera from cattle infected with *Fasciola hepatica* or with other common gastrointestinal parasites.

Rabbit anti-TCA2-MBP recognized the 10 kDa proteins in ThFAS, *T. crassiceps* and *T. saginata*.

Polynucleotide Molecule

On the basis of the genetic code, there exits a finite set of nucleotide sequences which can genetically code for a given amino acid sequence. All such equivalent nucleotide sequences are operable variants of the disclosed sequences, since all give rise to the same protein, having the same amino acid sequence, during the course of an in vivo transcription and translation. Consequently, all such variants are intended to be included in the scope of the present invention.

Two DNA sequences are "substantially homologous" when at least 70 to 90%, preferably 80 to 90% and most preferably 85%, of the nucleotides match over the defined length of the selected region that encodes for the antigen. Sequences which are substantially homologous can be identified in a Northern hybridization experiment under conditions defined for that particular system. Defining appropriate hybridization conditions is within the skill of the art. See, e.g., T. Maniatis et al., *Molecular Cloning: A Laboratory Manual,* Cold Spring Harbor Laboratory, 1982; *DNA Cloning: A Practical Approach,* Volumes I and II (Ed. D. N. Glover) IRL Press, Oxford, 1985.

The gene which encodes the antigen of the present invention can be derived from *Taenia crassiceps*. The gene encoding the antigen is obtained using standard cloning techniques (Sambrook, J. et al. *Molecular Cloning: A Laboratory Manual,* 2nd Edition, Cold Spring Harbor Press, Cold Spring Harbor, N.Y. (1989)). The gene is comprised of the polynucleotide DNA. Other polynucleotides can also be used to express the antigen and are intended to be within the scope of the present invention.

Thus, in a preferred embodiment, the present invention achieves polynucleotides having the sequence that encodes at least part of the antigen having the homologous segment of the antigen isolated from *Taenia crassiceps*.

Expression Vehicles and Transformed or Transfected Host Cells

The coding sequence can be contained in vectors which are operable as cloning vectors or expression vectors when inserted into an appropriate host. The expression vector may be for example a replicon, plasmid, bacteriophage, virus or hybrid thereof. Vectors used in practicing the invention are selected to be operable as cloning vectors or expression vectors in the selected host cell. Numerous cloning vectors are known to those skilled in the art, and selection of an appropriate cloning vector is a matter of choice. Examples of cloning vectors include bacteriophage lambda gt11, pBR 322, pUC18, and pIH821. See generally, *DNA Cloning*, Volumes I and II, supra, and Maniatis et al., supra. Additionally, the present invention encompasses the use of eukaryotic and other procaryotic cloning vectors. The expression vector is then inserted in host cells. A variety of vector-host combinations may be used.

The encoding DNA or expression vector of the present invention can be expressed in mammalian cells or other eukaryotic cells, such as yeast, or in prokaryotic cells, in particular bacteria. A number of approaches may be taken for evaluating optimal expression plasmids for the expression of cloned cDNAs in yeast [see Glover, D. Ed., *DNA Cloning*, Vol. II, pp. 45–66, IRL Press (1985)]. Bacterial strains may also be utilized as hosts for the production of the antigens of the present invention, such as *E. coli* strains PR722 and Y1090, and other enterobacteria such as Salmonella, Serratia and Pseudomonas.

Method to Produce and Purifiy the Protein Using the Recombinant Cells

Mass production of antigen by recombinant DNA synthesis offers an attractive solution to the antigen supply problem once a reactive antigen has been identified. The recombinant antigen can be easily purified to homogeneity, in high quantities and at relatively little expense without the need to use laboratory rodents for propagation in diagnostic application.

Commercial kits are available for producing and purifying a fusion protein such as those available from New England BioLabs. The process generally comprises the following steps of inoculating broth containing glucose and ampicillin with cells containing the fusion plasmid; grow the cells; add IPTG; incubate the cells at 37° C. for 1 to 3 hours; harvest the cells by centrifugation; resuspend the cells; freeze overnight; thaw; sonicate to break open the cell; centrifuge; separate using an amylose resin; elute the fusion protein with buffer and maltose; collect fractions; pool the protein containing fractions; and concentrate.

Method of Diagnosing Bovine or Swine Cysticercosis

The development of accurate and reliable serological screening methods would be expected to result in improved efficiency of inspection procedures and reduced cost. The antigen of the present invention is useful for immunoassays which detect or quantitate the presence of *Taenia saginata* and/or *Taenia solium* in a sample, preferably serum. The immunoassay using the present invention typically comprises incubating a biological sample in the presence of an antigen of the present invention, forming an immunocomplex and detecting the complex. Various immunoassays procedures are described in *Immunoassays for the 80's*, Voller, A. et al., eds. University Park, 1981.

One of the ways antibodies to the antigen of the present invention can be detected is by the use of an enzyme immunoassay(EIA), or enzyme-linked immunosorbent assay (ELISA). This enzyme, when exposed to the substrate, will react and generate a chemical moiety which can be detected, for example by spectrophotometric, fluorometric or visual means. Modifications of the immunoassay include choice of solid-phase carrier surfaces, coupling or coating buffer, blocking agent, enzyme-conjugated antisera, substrate, color indicator and test configuration. Test configurations in ELISA includes use of either a double- or triple (amplified) antibody sandwich test system.

By radioactively labeling the antigen of the present invention, it is possible to use radioimmunoassay (RIA) as a method of diagnosing cysticercosis. It is also possible to use fluorescent labels, chemiluminescent labels, and bioluminescent labels.

Further, the test configuration may be a one step, two step or sandwich assay. See, for example Work, T. et al., *Laboratory Techniques and Biochemistry in Molecular Biology*, North Holland Publishing Company, N.Y. (1978).

In one aspect of the invention, the antigen may be added to a solid support which is capable of immobilizing particles such as the proteins of the present invention. Well-known supports or carriers include glass, polystyrene, polypropulene, polyethylene, dextran, nylon, natural and modified celluloses, polyacrylamides, and agaroses. The support material may have any possible structural configuration so long as it is capable of binding to a protein. Thus, the support configuration may be spherical, as in a bead, or cylindrical, as in the inside surface of a test tube, or the external surface of a rod. Alternatively, the surface may be flat, such as a sheet or test strip. Those skilled in the art will know many other suitable carriers for binding the antigen, or will be able to ascertain the same by the use of routine experimentation.

The binding activity of any given lot of the antigen may be determined according to well known methods. Those skilled in the art will be able to determine operative and optimal assay conditions by employing routine experimentation.

The following examples are offered to illustrate the present invention and are not intended to limit the scope of the invention.

EXAMPLE I

Isolation and Characterization of Novel Antigen from *Taenia crassiceps* as Well as Antigen from *Taenia saginata*

*T. crassiceps* (HYG mouse strains) were maintained in female Swiss-Webster mice. Mice were inoculated intraperitoneally with 8 to 10 metacestodes suspended in a small amount of saline. Parasites were harvested at 30 to 60 days post-infection by flushing the opened peritoneal cavity with saline. The metacestodes were washed in saline, suspended in 50 mM Tris/HCl buffer, pH 7.5 and homogenized using a Teflon on glass tissue grinder. The homogenate was centrifuged at 17000×g for 20 minutes and the supernatant treated with ammonium sulfate as described for ThFAS [Rhoads, M. et al., *J. Parasit.*, 71:774–787 (1985)]. The protein fraction was labeled TcAS.

A similarly prepared ammonium sulfate-soluble fraction from viable *T. saginata* metacestodes excised from the tissues of experimentally-infected calves was designated TsAS [Kamanga-Sollo et al., *Proc. Am. Assoc. Vet. Res.* 48:1206–1210 (1987)].

EXAMPLE II

DNA Sequencing

*Taenia crassiceps* were maintained in Swiss-Webster white mice by serial passage. Cysts were recovered 2–3 months after infection from the peritoneal cavity of the sacrificed mice and washed by settling through several changes of phosphate buffered saline (PBS).

Total RNA was isolated from *T. crassiceps* mestacestode cysts by a modification of the quanidinium isothiocyanate:

cesium trifluoracetate procedure described by Okayama et al., *Methods of Enzymol. Vol.* 154 (1987). Approximately 100 ml of settled cysts recovered from three mice were passed through a 20 ga. needle to break the cysts open. The tissue was centrifuged 5 minutes at 3500 rpm then washed several times in phosphate buffered saline. The final pellet was suspended in 30 ml of solution containing 50 mM TRIS, pH 8.0, 100 mM sodium chloride and 50 mM EDTA and treated with 2% sodium dodecyl sulfate and 1 mg/ml proteinase K for 1 hour at 65° C. The digested tissue was extracted three times with phenol:chloroform:isoamyl alcohol (25:24:1) and the nucleic acids precipitated in 0.3M sodium acetate and 2.5 volumes of ethanol. The precipitated nucleic acids were then separated according to Okayama where the RNA was pelleted through a cesium trifluoracetate:quanidinium isothiocyanate centrifugation gradient. The RNA which pelleted at the bottom of the gradient was washed with 70% ethanol (3×1.0 ml) and redissolved in sterile TE (10 mM TRIS, pH 7.6, 1 mM EDTA). No further purification was performed.

Poly A mRNA was isolated by two successive passes of total RNA through an oligo (dT)-cellulose column essentially as described by Aviv et al., *Proc. Natl. Acad. Sci. USA* 69:1408–1412 (1972). The poly A mRNA was eluted from the oligo (dT) cellulose column with sterile water preheated to 65° C. and then precipitated in 0.3M sodium acetate and 2.5 volumes of ethanol. The poly A mRNA was pelleted by centrifugation, washed with 80% ethanol, centrifuged once again, dried in vacuo, and dissolved in water.

Double stranded cDNA was generated from 10 μg of purified poly A mRNA according to the method of Gubler et al., *Gene* 25:263–269 (1983), as modified by Watson et al., *DNA Cloning*, Vol. I, Ed. D. M. Glover, IRL Press, Oxford, pages 79–88 (1985) using Eco RI linkers. In brief, first strand cDNA synthesis was carried out in 55 μl by priming with oligo dT in the presence of RNAsin, the appropriate dNTPs, and Avian Myoblastosis Virus (AMV) reverse transcriptase. cDNA synthesis was stopped after 1 hour at 42° C. and the solution containing cDNA-RNA hybrid was directly treated for second strand synthesis. Second strand synthesis was carried out in 250 μl in the presence of dNTPs, RNase H and DNA polymerase I. After a 1 hour incubation at 14° C. followed by a 1 hour incubation at room temperature (22° C.), the reaction was halted and the double stranded cDNA was methylated with S-adenosyl-L-methionine by Eco RI methylase and the cDNA ends made blunt by treatment with T4 DNA polymerase in the presence of dNTP. After phenol-chloroform extraction, ethanol precipitation, centrifugation, and drying in vacuo, Eco RI linkers were ligated to the methylated cDNA termini using T4 DNA ligase and RNA ligase. The cDNA was then digested with Eco RI restriction enzyme for 1 hour at 37° C. to produce Eco RI compatible ends on the cDNA. The reaction was stopped with EDTA, phenol-chloroform extracted, ethanol precipitated, collected by centrifugation, dried in vacuo, resuspended in TE, and passed over a "NACS" column (Bethesda Research Laboratories). The cDNA was eluted in 2M NaCl in TE, ethanol precipitated, collected by centrifugation, dried in vacuo and resuspended in TE.

Ten percent of the double-stranded cDNA was ligated to 1 μg of lambda-gt11 arms containing compatible Eco RI ends using T4 DNA ligase at 14° C. for 16 hours.

The *Taenia crassiceps* cDNA-bacteriophage DNA was packaged into intact virus particles using a "Packagene" extract following the procedures described by the manufacture (Promega Biotech). After packaging, *E. coli* strain Y1090 was infected with the packaged cDNA library and plated onto Luria Broth (LB) agar plates in LB agarose containing 0.2% X-gal, 0.1 mM IPTG, and 100 μg/ml ampicillin. Using this technique, greater than 95% of the bacteriophage were observed to be recombinant (i.e., contained cDNA inserts) as judged by the percentage of white plaques of the total plaques obtained.

In order to screen the cDNA libraries, anti-sera was generated by inoculating rabbits with *Taenia crassiceps*, TcAS antigen or with purified ThFAS antigen. Individual rabbits were inoculated subcutaneously with one of the protein preparation emulsified in Complete Freund's adjuvant and boosted two times further at 1 week intervals. Immune sera were collected after about 4 weeks.

Calf sera was obtained from animals experimentally-infected with *Taenia saginata* eggs ranging from as few as 1000 eggs per animal to as high as 100,000 eggs per animal.

Aliquots of the *T. crassiceps* bacteriophage library were used to infect and transform (transfect) *E. coli* Y1090 and were plated out on LB ampicillin plates. [See Young R. et al., *Proc. Natl. Acad. Sci. USA* 80:1194–1198 (1983) and *Science* 222:778–782 (1983)]. The plates containing developing phage plaques were overlaid with nitrocellulose membrane disks which had been soaked in 10 mM IPTG and were incubated at 42° C. for 3 hours to induce production of the β-galactosidase fusion protein then transferred to 37° C. The nitrocellulose disks, impregnated with the *E. coli* proteins containing putative recombinant fusion protein, were removed from the plates after overnight incubation at 37° C., blocked in immunowash buffer (IWB) (0.15M sodium chloride, 50 mM TRIS, pH 7.8, 0.05% Tween-20, and 5% non-fat dried milk), then screened overnight with a 1:200 dilution of serum from either a calf experimentally-infected with *T. saginata* eggs or with rabbit anti-ThFAS sera. Peroxidase labeled rabbit anti-bovine IgG (1.0 μg/ml) or goat anti-rabbit IgG (1.0 μg/ml) were used as second antibodies, respectively. Positive clones (antibody binding) were visualized colormetrically with 4-chloro-1-naphthol and hydrogen peroxide and approximately 32 clones were picked and rescreened as described above using rabbit anti-ThFAS infection sera.

Nineteen putative positives were picked and rescreened with rabbit antiserum to parasite antigen (diluted 1:200) followed by peroxidase-labeled goat anti-rabbit IgG. Two of these clones showed strong hybridization in all the above screenings and were designated TCA-2 and TCA-12.

Once identified and removed from the respective culture plate, positive bacteriophage TCA-2 was plaque purified by several rounds of plating, screening and isolation as described above. This procedure was repeated until 100% of the plaques from the clone produced a positive signal upon immunoscreening. The approximate mass of the β-glactosidase fusion protein is 123,000 kDa of which 7.0 kDa is attributed to protein production from the TCA-2 gene.

TCA-2 was subcloned into plasmid vectors to facilitate further characterization by DNA mapping and DNA sequencing [Veira, J. et al., *Gene* 19:259–268 (1982) and Guan et al., *Gene* 67:21–30 (1987)]. See Table I for the DNA sequence of TCA-2. For subcloning procedures see generally, Maniatis et al., 1982, supra. In the cloning of TCA-2 DNA, the gene was inserted into the Eco RI restriction site of lambda-gt11. To transfer this gene into the plasmid vectors, the TCA-2 sequence in lambda-gt11 was first amplified using polymerase chain reaction (PCR) as defined in the Perkin-Elmer Cetus GENE AMP™ DNA Amplification Reagent Kit. PCR was performed using 2.5 ng of the TCA 2:lamda-gt11 hybrid DNA purified according to Maniatis et al., 1982 supra, and using the lambda DNA primers 5' GGTGGCGACGACTCCTGGAGCCCG (SEQ ID NO:3) and 5' TTGACACCAGACCAACTGGTAATG (SEQ ID NO:4). The amplified TCA-2 sequence was digested with Eco RI endonuclease and ligated to the Eco RI sites of pUC18 and pIH821 plasmid DNAs as generally described by Maniatis et al., 1982, supra. The new vectors containing the TCA-2 gene were used to transform bacterial cells JM101 and PR722, respectively according to Hanahan, J. Mol. Biol. 166:557–580 (1983). Cells containing the TCA-2 insert were assayed both by agarose gel electrophoresis relative to plasmid DNA without TCA-2 inserted and by antibody screening using rabbit anti-ThFAS antisera as described above for screening the cDNA library.

For labeling and hybridization studies, plasmid DNA was used both labeled as is or digested with Eco RI, electrophoresed on LMP agarose (FMC) and the TCA-2 insert DNA excised from the gel and purified away from the rest of the plasmid. The insert DNA was labeled with 100 µCi of $^{32}$P-alpha dCTP (3000 µCi/mMole, New England Nuclear) by nick translation, Rigby et al. J. Mol. Biol. 113:237 (1977) using DNase I and DNA polymerase I (BRL). Labeled DNA was separated from $^{32}$P-dCTP by spun column chromatography as described by Maniatis et al., 1982, supra. T. crassiceps DNA was purified as described by Dame, J. et al., Molecular and Biochemical Parasitology 8:263–279 (1983). The purified DNA (10 µg) was digested with either DRA I, Eco RI or Hind III restriction enzymes (BRL), electrophoresed in 0.8% agarose (FMC) and transferred to "Nytran" membrane using Southern blotting procedures (see Southern, E., J. of Molecular Biology 98:503–517 (1975)). After transfer, the DNA-blotted "Nytran" paper was linked to the membrane by using UV light then prehybridized with 0.5M NaCl, 0.05M sodium citrate, pH 7.0 (6× SSC), Denhardt's solution, and 0.2% sodium dodecyl sulfate (SDS) for 6 hours at 65° C. The blots were washed three times with 0.2× SSC, 0.1% SDS at 50° C. for 30 minutes per wash. The blots were air dried and overlaid with photographic film (Kodak XAR) to visualize the hybridization patterns.

Figure 2:
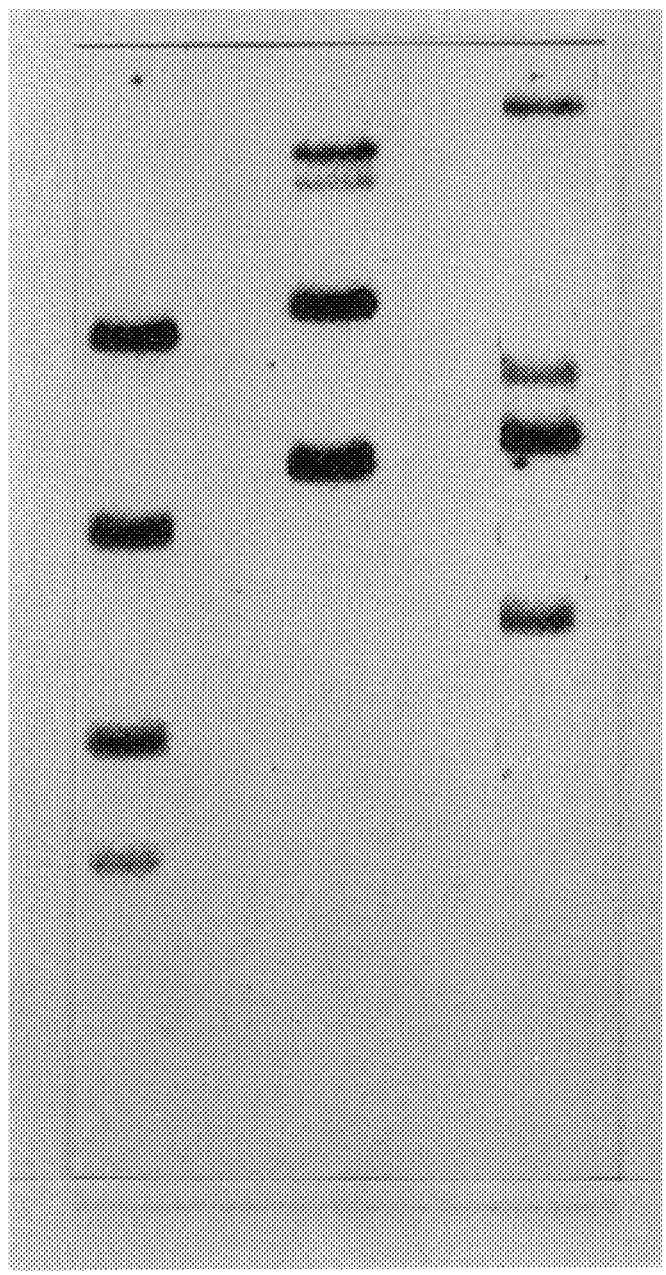
FIG. 2 is a Southern blot of restriction enzyme digests of *T. crassiceps* genomic DNA probed with TCA-2 sequence. Channel one enzyme is DRA-I; channel two is the plasmid only; channel three is Eco RI (with plasmid contaminate); channel four is blank; and channel five is Hind III.
Figure 3:
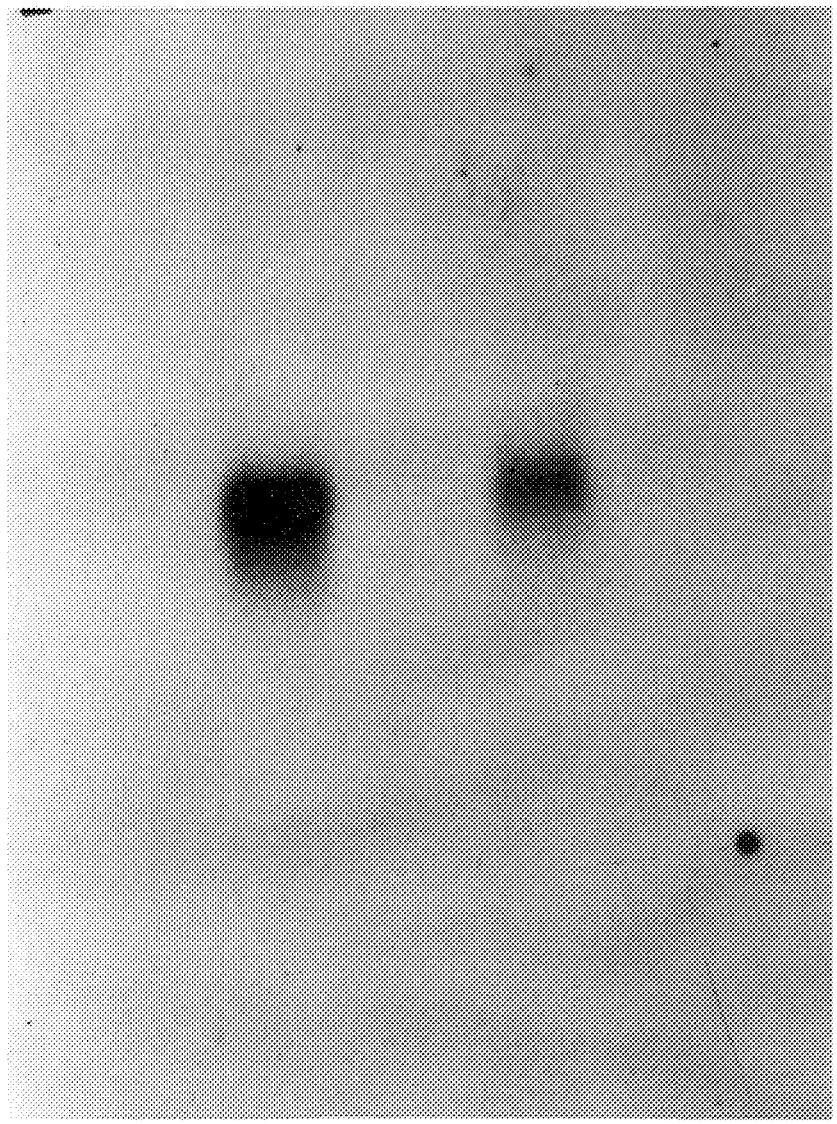
FIG. 3 is a Northern blot of the total RNA on a formaldehyde gel. Channel one is the total RNA extracted from *T. crassiceps* and channel two is from *T. saginata*.

The Southern blot restriction enzyme digests of T. crassiceps genomic DNA probed with TCA-2 sequence is shown in FIG. 2. Channel 1 enzyme is with DRA-I; channel 2 is plasmid only; channel 3 is Eco RI (with plasmid contaminated buffer); channel 4 is a blank; and channel 5 is with Hind III.

Northern blots were similarly generated using the 10 µg of total RNA isolated from T. crassiceps cysts and separated on a 1% denaturing formaldehyde gel as described by Davis, L. et al., Basic Methods in Molecular Biology, Elsevier Science Publishing Co., Inc. (1986). After separation on 1% agarose the RNA was transferred to NYTRAN and screened with insert TCA-2 cDNA as described above for Southern blot analysis. See FIG. III. Channel one contains total RNA isolated from T. crassiceps and channel two contains total RNA isolated from T. saginata.

The foregoing techniques including the sequencing described earlier indicate that the TCA-2 cDNA insert is 288 bp in length and contains sequences coding for a ribosome binding site, poly A signal sequence, poly A tail and both start and stop translation codons. Furthermore, the gene is likely to be single copy as evidenced by single bands which appeared with each restriction enzyme on the probed membranes (Southern blots).

Positive signals on probed Northern blots of RNA from T. crassiceps cysts suggest the TCA-2 is encoded by a single messenger RNA species which is approximately 450–500 bases in length.

TABLE 1

SEQ ID NO:2

| | |
|---|---:|
| GAATTCCATAAGGGACCTGAGGATCTGAAGAAGAAAATGATGAAGCAATTGGGTGAGGTG | 60 |
|                                                               M  M  K  Q  G  L  E  V | |
| CGTCGCTTCTTCAGGGAGGATCCTCTGGGCCAGAAGATTATTGACCATTTCCAAGAGACG | 120 |
| R  R  F  F  R  E  D  P  L  G  Q  K  I  I  D  H  F  Q  E  T | |
| GTCTCTATCTGCAAGGCCATCAGAGAGCGGATAAGAAAACGCCTTGGAGAATACCTAAAG | 180 |
| V  S  I  C  K  A  I  R  E  R  I  R  K  R  L  G  E  Y  L  K | |
| GGTCTTGAAAATGAATAGATGTTGAGTTAAATCCACAAGGAAAAGTGATTAAATAAAAGG | 240 |
| G  L  E  N  E  - | |
| AACTCTTTCCCAGCAAAAAAAAAAAAAAAAAAAAAAAAAAAAAAAGG | 288 |

TCA-2 DNA sequence. Total number of bases is 288. Analysis done on the complete sequence. Done on (absolute) phase(s): 1. Using the universal genetic code.

EXAMPLE III

Expression Vehicles

The coding sequence from one ThFAS-positive clone from Example II, designated TCA-2, which also reacted specifically with cysticercosis-infected bovine sera, was subcloned into the Eco RI site of the expression plasmid pIH 821 and used to transform E. coli PR722. The plasmid was renamed pTCA2.

EXAMPLE IV

Method to Produce the Protein Using the Recombinant Cells

The plasmid-transformed PR722 cells are grown overnight in LB medium containing isopropyl-B-D-thiogalactosidase then treated with lysozyme to a final concentration of 0.5 mg/ml for 5 minutes on ice and sonicated. The lysed cells release the maltose-binding TCA-2 fusion protein into solution. As the TCA-2 gene is fused to the maltose-binding gene, induction of the production of the maltose-binding protein will produce the TCA-2 antigen as well, if the TCA-2 gene is cloned in the correct reading frame and correct orientation relative to the reading frame of the maltose-binding protein gene and the reading frame of the TCA-2 gene sequences in nature.

EXAMPLE V

Purification of Fusion Protein

The ThFAS positive clone from Example III, TCA-2 was subcloned into the Eco RI site of the expression plasmid pIH 821 and used to transform *E. coli* PR722. The plasmid was renamed pTCA 2. Transformed cells containing the plasmid pTCA 2 were grown at 37° C. to mid-log phase, and the maltose-binding fusion protein induced with isopropyl B-D-thiogalactopyranoside (IPTG) (0.3 mM) for 2 hours. The cells were pelleted, resuspended in lysis buffer (10 mM Tris, pH 7.2, 30 mM sodium chloride, 10 mM EDTA, 10 mM EGTA, and 0.25% Tween-20) then frozen overnight. The next day, the thawed cells were sonicated, centrifuged at 9000×g for 30 minutes and the supernatant passed over an amylose resin affinity column previously equilibrated in lysis buffer. The column was extensively washed with lysis buffer without Tween-20 and the bound fusion protein eluted in the same buffer supplemented with 10 mM maltose. Fractions containing the fusion protein were pooled and used for ELISA and Western blot analysis.

Northern blots. Total RNA from *T. crassiceps* metacestodes and *T. saginata* proglottids was electrophoresed on 1% formaldehyde gels and transferred to Nytran membranes essentially as described by Davis et al. The blots were hybridized overnight at 65° C. to pTCA-2 probe radiolabeled by nick translation then washed at 50° C. (4×20 min) in 0.1% SDS and 0.2% SSC (1× SSC is 0.15M sodium chloride, 0.015M sodium citrate, pH 7.0) and autoradiographed.

Rabbit and cattle antisera. ThFAS, TcAS and fusion protein TCA2-MBP were injected (3×200 $\mu$g protein/dose) subcutaneously at 3 week intervals into New Zealand female adult rabbits. Protein samples were emulsified prior to injection in both Freund's complete adjuvant (first injection) and Freund's incomplete adjuvant (second and third injections). Serum was collected before inoculation and one week after the final inoculation. Rabbit antiserum to maltose-binding protein (MBP) was supplied by the manufacturer (New England Biolabs).

Serum samples from cattle experimentally-infected with *T. saginata* (Exp-I) were obtained elsewhere at 13 to 26 weeks post-infection. Experimentally-uninfected (Exp-U) serum samples were obtained from the same animals prior to infection. Pooled sera from cattle with naturally-acquired infections of *Fasciola hepatica* (Fc-I) was obtained from Louisiana State University. Cattle serum from animals harboring common gastrointestinal parasites of the genera Moniezia, Ostertagia, Haemonchus, Cooperia, and Nematodirus (gp-I) was obtained from the U.S. Department of Agriculture.

Western immunoblots. Polyacrylamide gel electrophoresis and protein transfer to Immobilon PVDF membranes (Millipore) were performed essentially as described using 6 to 15% acrylamide gradient gels. After transfer, membranes were blocked for 1 hour with 0.01M PBS containing 1% bovine serum albumin. When bovine antisera was tested, 5% normal rabbit serum was included in the blocking reagent. Membranes were incubated in test antisera diluted 1/100 for at least 2 hours followed by a 1-hour incubation with 1/1000 dilutions of either goat anti-rabbit IgG or rabbit anti-bovine IgG peroxidase conjugates. Membranes were washed 5 times with PBS-0.02% Tween after each incubation then visualized with hydrogen peroxide and 4-chloro-1-naphthol substrate solution.

ELISA. One microgram of antigen (ThFAS, TcAS, TCA2-MBP, or MBP) was diluted in 0.01M sodium carbonate buffer, pH 9.6, and 100-$\mu$l aliquots were added to wells of an ELISA plate. Wells were blocked, and screened as described above. The absorbance of the peroxidase reaction (determined with 2-2-azino-di-[3-ethyl-benzothiazoline sulfonic acid and hydrogen peroxide) was measured at 405 nm.

ThFAS contains a group of high molecular weight proteins (65 to 77 kDa) and a low molecular weight protein of 10 kDa where the 10 kDa protein was identified as the *T. saginata*- reactive, immunodiagnostic component. TcAS contains a related 10 kDa protein that is recognized by anti-ThFAS serum; however, the high molecular weight ThFAS-cross-reactive proteins were not present in TcAS. Conversely, rabbit anti-TcAS specifically recognized the 10 kDa protein (appearing as a doublet) in ThFAS and TsAS, as well as the homologous antigen, TcAS, but did not cross-react with any high molecular weight antigens. Western blots indicated that the 10 kDa TcAS protein binds *T. saginata* antibodies (Exp-I) and is not recognized by Exp-U serum.

Primary screening of the *T. crassiceps* cDNA clones with rabbit anti-ThFAS serum identified at least 32 strongly reactive plaques. One phage, designated TCA-2, generated a β-galactosidase fusion protein with an apparent molecular weight of 120–130 kDa and reacted specifically with cysticercosis-infected bovine sera. The coding sequence, estimated to be 288 bp in length, was subcloned into the Eco RI site of the expression plasmid pIH 821 resulting in the production of a maltose-binding fusion TCA 2-MBP. When total protein from IPTG induced cells was compared to protein from uninduced pTCA-2 transformed cells, the IPTG-induced cells gave rise to an additional protein band with a molecular weight of 47 kDa. Following adsorption of the cell extract from induced cells to an amylose-resin affinity column, and washing with column buffer, a 47 kDa fusion protein was eluted in 10 $\mu$M maltose on SDS-PAGE. Rabbit anti-ThFAS did not react with proteins from uninduced cell extracts, but did react with TCA 2-MBP present in crude extracts and the affinity purified cell fraction. The 47 kDa protein was recognized by rabbit anti-MBP (maltose-binding protein).

Northern blots probed with radiolabeled pTCA-2 indicated that the TCA-2 encoding mRNA was approximately 450–500 bases in length and demonstrated hybridization of TCA-2 DNA sequence to RNA purified from adult *T. saginata*.

Rabbit antibodies generated against TCA2-MBP were used to identify immunologically cross-reactive 10 kDa antigens in *T. crassiceps, T. hydatigena* and *T. saginata*.

The efficacy of TCA 2-MBP to detect experimentally infected animals was assessed by both Western blot analysis and ELISA. All Exp-I sera reacted strongly with TCA2-MBP on Western blots where no reaction with Fc-I, gp-I, Exp-U sera was observed. None of the sera reacted with MBP.

ELISA. TCA2-MBP was able to detect all 10 Exp-I sera when compared to Exp-U sera. Threshold absorbance values were determined by the mean absorbance of the Exp-U plus 2 standard deviations. Fc-I and gp-I sera did not react above threshold values. MBP did not react with any of the EXP-I sera.

The foregoing description of the specific embodiments reveals the general nature of the invention and others can by applying current knowledge, readily modify and/or adapt such specific embodiments without departing from the inventive concept and therefore such adaptations and modifications should be and are intended to be comprehended within the meaning and range of equivalents of the disclosed embodiments. It is to be understood that the phraseology or terminology employed herein is for purposes of description and not of limitation.

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 288 base pairs
        ( B ) TYPE: nucleic acid
        ( C ) STRANDEDNESS: double
        ( D ) TOPOLOGY: unknown ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Taenia crassiceps
        ( B ) STRAIN: HYG
        ( D ) DEVELOPMENTAL STAGE: Metacestode ( i x ) FEATURE:
        ( A ) NAME/KEY: CDS
        ( B ) LOCATION: 37..195

( x i ) SEQUENCE DESCRIPTION: SEQ ID NO:1:

```
GAATTCCATA AGGGACCTGA GGATCTGAAG AAGAAA ATG ATG AAG CAA TTG GGT        54
                                         Met Met Lys Gln Leu Gly
                                          1               5

GAG GTG CGT CGC TTC TTC AGG GAG GAT CCT CTG GGC CAG AAG ATT ATT       102
Glu Val Arg Arg Phe Phe Arg Glu Asp Pro Leu Gly Gln Lys Ile Ile
             10                  15                  20

GAC CAT TTC CAA GAG ACG GTC TCT ATC TGC AAG GCC ATC AGA GAG CGG       150
Asp His Phe Gln Glu Thr Val Ser Ile Cys Lys Ala Ile Arg Glu Arg
         25                  30                  35

ATA AGA AAA CGC CTT GGA GAA TAC CTA AAG GGT CTT GAA AAT GAA           195
Ile Arg Lys Arg Leu Gly Glu Tyr Leu Lys Gly Leu Glu Asn Glu
     40                  45                  50

TAGATGTTGA GTTAAATCCA CAAGGAAAAG TGATTAAATA AAAGGAACTC TTTCCCAGCA     255

AAAAAAAAAA AAAAAAAAA AAAAAAAAA AGG                                    288
```

( 2 ) INFORMATION FOR SEQ ID NO:2:

( i ) SEQUENCE CHARACTERISTICS:
        ( A ) LENGTH: 53 amino acids
        ( B ) TYPE: amino acid
        ( D ) TOPOLOGY: linear ( i i ) MOLECULE TYPE: protein (x i) SEQUENCE DESCRIPTION: SEQ ID NO:2:

| Met | Met | Lys | Gln | Leu | Gly | Glu | Val | Arg | Arg | Phe | Phe | Arg | Glu | Asp | Pro |
| 1 | | | | 5 | | | | | 10 | | | | | 15 | |

| Leu | Gly | Gln | Lys | Ile | Ile | Asp | His | Phe | Gln | Glu | Thr | Val | Ser | Ile | Cys |
| | | | 20 | | | | | 25 | | | | | 30 | | |

| Lys | Ala | Ile | Arg | Glu | Arg | Ile | Arg | Lys | Arg | Leu | Gly | Glu | Tyr | Leu | Lys |
| | | | 35 | | | | 40 | | | | | 45 | | | |

| Gly | Leu | Glu | Asn | Glu |
| | 50 | | | |

(2) INFORMATION FOR SEQ ID NO:3:

(i) SEQUENCE CHARACTERISTICS:
        (A) LENGTH: 24 base pairs
        (B) TYPE: nucleic acid
        (C) STRANDEDNESS: single
        (D) TOPOLOGY: unknown (i i) MOLECULE TYPE: DNA (genomic)

(i i i) HYPOTHETICAL: NO (i v) ANTI-SENSE: NO (v i) ORIGINAL SOURCE:
        (A) ORGANISM: Taenia crassiceps
        (B) STRAIN: HYG
        (D) DEVELOPMENTAL STAGE: Metacestode (x i) SEQUENCE DESCRIPTION: SEQ ID NO:3:

GGTGGCGACG ACTCCTGGAG CCCG       24

(2) INFORMATION FOR SEQ ID NO:4:

(i) SEQUENCE CHARACTERISTICS:
        (A) LENGTH: 24 base pairs
        (B) TYPE: nucleic acid
        (C) STRANDEDNESS: single
        (D) TOPOLOGY: unknown (i i) MOLECULE TYPE: DNA (genomic)

(i i i) HYPOTHETICAL: NO (i v) ANTI-SENSE: NO (v i) ORIGINAL SOURCE:
        (A) ORGANISM: Taenia crassiceps
        (B) STRAIN: HYG
        (D) DEVELOPMENTAL STAGE: Metacestode (x i) SEQUENCE DESCRIPTION: SEQ ID NO:4:

TTGACACCAG ACCAACTGGT AATG       24

We claim:

1. An isolated DNA segment comprising a DNA sequence which encodes the *Taenia crassiceps* 10 kDa antigen comprising an amino sequence as set forth in SEQ ID NO.2, said antigen being effective for binding antibodies made in a host to *Taenia saginata* and/or *Taenia solium*.

2. The DNA segment of claim 1 wherein said DNA sequence has the following nucleotide sequence:

GAATTCCATAAGGGACCTGAGGATCTGAAGAAGAAAATGATGAAGCAATTGGGTGAGGTG   60

CGTCGCTTCTTCAGGGAGGATCCTCTGGGCCAGAAGATTATTGACCATTTCCAAGAGACG   120

GTCTCTATCTGCAAGGCCATCAGAGAGCGGATAAGAAAACGCCTTGGAGAATACCTAAAG   180

-continued

CGTCTTGAAAATGAATAGATGTTGAGTTAAATCCACAAGGAAAAGTGATTAAATAAAAGG 240

AACTCTTTCCCAGCAAAAAAAAAAAAAAAAAAAAAAAAAAAAAAAAGG 288 (SEQ ID NO:1).

3. A recombinant polynucleotide segment comprising: a first DNA sequence encoding the *Taenia crassiceps* 10 kDa antigen comprising the amino acid sequence as set forth in SEQ ID NO. 2, said antigen being effective for binding antibodies made in a host to *Taenia saginata* and/or *Taenia solium;* and a second nucleotide sequence heterologous to said first DNA sequence wherein said first and second sequence are in operable linkage to each other.

4. A polynucleotide segment according to claim 3, wherein said first DNA sequence has the following nucleotide sequence:

GAATTCCATAAGGGACCTGAGGATCTGAAGAAGAAAATGATGAAGCAATTGGGTGAGGTG 60

CGTCGCTTCTTCAGGGAGGATCCTCTGGGCCAGAAGATTATTGACCATTTCCAAGAGACG 120

GTCTCTATCTGCAAGGCCATCAGAGAGCGGATAAGAAAACGCCTTGGAGAATACCTAAAG 180

CGTCTTGAAAATGAATAGATGTTGAGTTAAATCCACAAGGAAAAGTGATTAAATAAAAGG 240

AACTCTTTCCCAGCAAAAAAAAAAAAAAAAAAAAAAAAAAAAAAAAGG 288 (SEQ ID NO:1).

5. A polynucleotide segment according to claim 3, wherein said second nucleotide sequence is the bacteriophage lambda gt11.

6. A polynucleotide segment according to claim 3, wherein said second nucleotide sequence is the plasmid pUC18.

7. A polynucleotide segment according to claim 3, wherein said second nucleotide sequence is the plasmid pIH821.

8. An expression vector comprising the polynucleotide segment according to claim 3.

9. The expression vector according to claim 8, wherein said vector is a plasmid, bacteriophage, virus, or hybrid thereof.

10. An isolated host cell transformed or transfected with the molecule according to claim 8.

11. An isolated host cell transformed or transfected with the molecule according to claim 9.

12. The isolated transformed host cell according to claim 10, wherein said host cell is a cell selected from the group consisting of a eukaryotic cell, prokaryotic cell, bacterial cell, and *Escherichia coli*.

13. The isolated host cell according to claim 10, wherein the host cell which is transformed or transfected is PR722.

14. A method of producing the *Taenia crassiceps* 10 kDa antigen comprising:
(a) culturing the isolated transformed host cell according to claim 10;
(b) expressing said antigen; and
(c) recovering said expressed antigen.

* * * * *